United States Patent [19]

Kummer et al.

[11] 4,256,909

[45] Mar. 17, 1981

[54] PREPARATION OF DIMETHYL BUTANEDICARBOXYLATES

[75] Inventors: Rudolf Kummer, Frankenthal; Heinz-Walter Schneider, Ludwigshafen; Franz-Josef Weiss, Weinheim; Otto Lemann, Weisenheim, all of Fed. Rep. of Germany

[73] Assignee: BASF Aktiengesellschaft, Fed. Rep. of Germany

[21] Appl. No.: 66,552

[22] Filed: Aug. 15, 1979

[30] Foreign Application Priority Data

Aug. 30, 1978 [DE] Fed. Rep. of Germany ....... 2837815

[51] Int. Cl.³ .............................................. C07C 67/38
[52] U.S. Cl. ..................................... 560/204; 560/233
[58] Field of Search .............................. 560/204, 233

[56] References Cited

U.S. PATENT DOCUMENTS

| | | |
|---|---|---|
| 3,481,975 | 12/1969 | Rudkousky . |
| 3,507,891 | 4/1970 | Hearne ................................. 560/233 |
| 3,778,466 | 12/1973 | Matswda .............................. 560/204 |
| 3,856,832 | 12/1974 | Ethyl Corp. ......................... 560/204 |
| 3,876,695 | 4/1975 | Kutepow . |
| 3,980,683 | 9/1976 | Isa ........................................ 560/233 |
| 4,041,057 | 8/1977 | Fanning .............................. 560/233 |
| 4,169,956 | 10/1979 | Kummer .............................. 560/204 |

FOREIGN PATENT DOCUMENTS

| | | |
|---|---|---|
| 2447068 | 4/1975 | Fed. Rep. of Germany ........... 560/233 |
| 2504005 | 8/1975 | Fed. Rep. of Germany ........... 560/233 |
| 2646955 | 4/1978 | Fed. Rep. of Germany ........... 560/204 |

*Primary Examiner*—Natalie Trousof
*Assistant Examiner*—Michael Shippon
*Attorney, Agent, or Firm*—Keil & Witherspoon

[57] ABSTRACT

In a process for the preparation of dimethyl butanedicarboxylates, wherein
(a) butadiene or a hydrocarbon mixture containing butadiene is reacted with carbon monoxide and methanol in the presence of a tertiary nitrogen base and a cobalt carbonyl catalyst at from 80° to 150° C. under superatmospheric pressure,
(b) the greater part of the tertiary nitrogen base and any excess hydrocarbons are removed and
(c) the methyl pentenoate thus obtained is reacted with carbon monoxide and methanol, in the presence of a cobalt carbonyl catalyst and the residual amount of tertiary nitrogen base, at from 140° to 200° C. under superatmospheric pressure, to give the dimethyl butanedicarboxylate, the improvement that the reaction mixture obtained in stage (a) after reaction of the butadiene is cooled until it separates into two phases, and a part-stream of from 20 to 80% by volume of the lower phase is recycled to stage (a).

5 Claims, No Drawings

PREPARATION OF DIMETHYL BUTANEDICARBOXYLATES

The present invention relates to a process for the preparation of dimethyl butanedicarboxylates, wherein butadiene or a hydrocarbon mixture containing butadiene is reacted with carbon monoxide and methanol in the presence of a tertiary nitrogen base and a cobalt carbonyl catalyst and, after removing the greater part of the tertiary nitrogen base, the methyl pentenoate thus obtained is reacted with methanol in the presence of the catalyst remaining in the reaction mixture, to give dimethyl butanedicarboxylates.

German Published Application DAS No. 2,037,782 discloses a process for the preparation of adipic acid in which butadiene, carbon monoxide and water are reacted under superatmospheric pressure in the presence of a rhodium compound as the catalyst. However, the yields thereby obtainable offer no encouragement to industrial operation of the process. In another process, described in German Published Application DAS No. 1,518,216, butadiene is reacted in the presence of cobalt carbonyl, pyridine and water under 430 bar at 210° C. to give dicarboxylic acids. The yield achieved is 50–70% of theory, based on butadiene. Further, Bull. Chem. Soc. of Japan, 46 (1973), 524–530 discloses that dimethyl adipate is obtained by reacting butadiene with carbon monoxide and methanol in the presence of cobalt carbonyl and pyridine and then carbonylating the resulting methyl pentenoate with the same catalyst, the temperature being raised to 240° C. in the second stage. The yields of dimethyl adipate are however only from 47 to 51%. A particular further disadvantage of all the processes is the low rate of reaction of butadiene to give the methyl pentenoate.

It is an object of the present invention to increase the reaction rate in the carbonylation of butadiene to give pentenoic acid esters without however involving increased amounts of catalyst in the steps of the preparation of the catalyst or in the subsequent steps of carbonylating the pentenoic acid esters to give adipic acid esters, and of recovering the catalyst.

We have found that this object is achieved by a process for the preparation of dimethyl butanedicarboxylates in which (a) butadiene or a hydrocarbon mixture containing butadiene is reacted with carbon monoxide and methanol in the presence of a tertiary nitrogen base and a cobalt carbonyl catalyst at from 80° to 150° C. under superatmospheric pressure, (b) thereafter the greater part of the tertiary nitrogen base and excess hydrocarbons are removed and (c) the resulting methyl pentenoate is then reacted with carbon monoxide and methanol in the presence of the residual amount of tertiary nitrogen base and cobalt carbonyl catalyst at from 140° to 200° C. under superatmospheric pressure to give dimethyl butanedicarboxylates, wherein the reaction mixture obtained in stage (a) after reaction of the butadiene is cooled until it separates into two phases, and a part-stream of from 20 to 80% by volume of the phase of greater density is recycled to stage (a).

The novel process has the advantage that the carbonylation of butadiene takes place more rapidly, but a higher cobalt content is not involved in the remaining stages.

The starting material is pure, 1,3-butadiene or a hydrocarbon mixture containing butadiene. Such hydrocarbon mixtures for example contain, in addition to butadiene, saturated hydrocarbons of 3 to 5 carbon atoms and monoolefinically unsaturated hydrocarbons of 3 to 5 carbon atoms. The butadiene content should as a rule be more than 10% by weight. In industry, $C_4$-cuts, in particular, are used as the starting mixture. Such cuts include any mixture of predominantly linear $C_4$-hydrocarbons which contain more than 10% by weight of 1,3-butadiene (simply referred to as butadiene) and more than 15% by weight of butenes. Depending on the origin of such mixtures, the individual components are present in the following proportions:

| Butadiene | 40–60% by weight |
|---|---|
| Isobutene | 20–35% by weight |
| But-1-ene | 10–25% by weight |
| But-2-ene | 5–15% by weight |
| Butanes | 1–10% by weight |
| Butynes | 0.1–3% by weight |

Such $C_4$-cuts are obtained, for example, from the dehydrogenation of butane or butene, or as by-products of the production of ethylene by thermal cracking of light naphtha or of higher hydrocarbon cuts.

The reaction is advantageously carried out with an excess of methanol, in particular with from 1.5 to 5 moles per mole of butadiene.

Preferably, the reaction is carried out at from 120° to 140° C. under a pressure of from 600 to 1,200 bar. As a rule, 0.05–0.15 gram atom of cobalt in the form of a cobalt carbonyl complex is used per mole of butadiene. Carbon monoxide is advantageously used in excess, for example in from 1.5 to 10 times the stoichiometrically required amount.

Suitable tertiary nitrogen bases advantageously have a $pK_a$ of 3–11, but should preferably be lower-boiling than the methyl pentenoate to be produced. Preferably, N-heterocyclic compounds such as pyridine ($pK_a$ 5.3), methyl pyridines, eg. 3-picoline ($pK_a$ 6.0) and isoquinoline ($pK_a$ 5.4), as well as trialkylamines, eg. trimethylamine ($pK_a$ 9.8) or triethylamine ($pK_a$ 11.0) are used. Pyridine has acquired particular industrial importance. It has proved particularly advantageous to use from 5 to 50 moles of pyridine per mole of cobalt carbonyl catalyst.

The cobalt catalysts used in stage (a) are advantageously introduced into the mixture as cobalt carbonyl, in particular as a solution in butadiene or in the $C_4$-cut. Such a solution is obtained, for example, by reacting an aqueous solution of a cobalt salt of a fatty acid, eg. an acetate or butyrate, with a mixture of carbon monoxide and hydrogen in the presence of active charcoal at from 100° to 170° C. under a pressure of from 100 to 400 bar. The resulting cobalt carbonyl is then extracted from the aqueous solution with butadiene or with the $C_4$-cut.

The reaction mixture obtained in stage (a) contains unconverted butadiene, other hydrocarbons where relevant, tertiary nitrogen base, cobalt carbonyl catalyst, excess methanol, the methyl pentenoate formed as the desired product, and by-products such as valeric acid esters, butyl ketones and butadiene polymers.

According to the invention, the reaction mixture obtained from stage (a) is cooled until it separates into two phases. This gives an upper phase of lower density, comprising the remaining hydrocarbons employed, and 70–95% by weight of methyl pentenoate, 60–85% by weight of nitrogen base, 10–40% by weight of methanol and 1–4% by weight of cobalt carbonyl catalyst, in each case based on total amount of material discharged from the reaction. Further, a lower phase of greater density is obtained, which contains virtually the entire catalyst (96–99% by weight), small amounts (5% by weight) of the hydrocarbons, 5–30% by weight of methyl pentenoate, 15–40% by weight of the nitrogen base and 60–90% by weight of the methanol. The phases are separated in the conventional manner, for example by decanting.

For the phase separation, it has proved advantageous to maintain a molar ratio of methyl pentenoate to methanol of from 1:0.05 to 1:0.5. Advantageously, the mixture is cooled to from −10° to +40° C., especially from −5° to +20° C.

It is furthermore advantageous if the cobalt carbonyl catalyst is no longer present as an allyl complex. This may be achieved, for example, by treating the reaction mixture, prior to the separation, for from 5 to 60 minutes with carbon monoxide at from 100° to 160° C. and under a pressure of from 5 to 200 bar.

A part-stream of 20–80% by volume, especially 50–70% by volume, of the lower phase of greater density is recycled to stage (a). Of course, the reaction conditions described above are set up for stage (a).

The hydrocarbons and the greater part of the pyridine are removed from the upper phase of lower density, for example by distillation.

The remainder of the upper phase is mixed with the remainder of the lower phase and the mixture is reacted in stage (c). In this stage, it is advantageous to maintain a molar ratio of methyl pentenoate to methanol of from 1:1.5 to 1:4. The reaction is carried out at from 140° to 200° C., especially from 150° to 180° C. Advantageously, pressures of from 100 to 400 bar are used. The reaction is carried out with carbon monoxide to which it is advantageous to add a few % by volume of hydrogen, for example from 0.2 to 4% by volume, in order to increase the rate of reaction. Further, it has proved advantageous if the reaction mixture contains from 2 to 10 moles of tertiary nitrogen base per mole of cobalt catalyst and from 0.01 to 0.08 mole of cobalt carbonyl complex per mole of methyl pentenoate. The reaction mixture obtained may for example be worked up as follows:

After releasing the pressure of the reaction mixture obtained in stage (c), excess methanol and free tertiary nitrogen base are distilled off. In this process, the tertiary nitrogen base bonded chemically to the catalyst (from 1 to 2 moles per gram atom of cobalt) is not distilled off. To avoid decomposition of the cobalt complex, with deposition of metallic cobalt, it has proved advantageous to pass a slow stream of carbon monoxide or of gases containing carbon monoxide into the distillation vessel of the column.

The residual reaction mixture, containing cobalt catalyst, dimethyl butanedicarboxylate and by-products is next treated with an oxidizing agent, such as molecular oxygen or a gas containing the latter, in particular air, in an aqueous acid medium, advantageously at a pH of from 3 to 6 and at from 80° to 160° C. After the treatment the mixture is separated into an organic and an aqueous phase, for example by decanting. Fractional distillation the organic phase gives residual tertiary nitrogen base, unconverted methyl pentenoate (which is recycled to the carbonylation) and a mixture of dimethyl butanedicarboxylates (80–85% by weight of dimethyl adipate, 11–15% by weight of dimethyl 2-methylglutarate and 3–6% by weight of dimethyl 2-ethylsuccinate). The ester mixture can be used for the preparation of diols or polyesters. The dimethyl adipate obtainable from the ester mixture by fractional distillation may be used for the preparation of adipic acid.

The aqueous phase, containing cobalt salts and free acid, is advantageously recycled to serve as the starting solution for the preparation of cobalt carbonyl.

The Examples which follow illustrate the process according to the invention.

EXAMPLE 1

(a) A mixture of 135.2 g of $C_4$-cut, containing 40 mole % of 1,3-butadiene (corresponding to 1.0 mole of 1,3-butadiene), 79.1 g (1.0 mole) of pyridine, 38.5 g (1.2 moles) of methanol and 0.04 mole of cobalt, in the form of cobalt carbonyl, per mole of 1,3-butadiene is reacted with carbon monoxide in a high pressure vessel of 0.5 liter capacity, at 135° C. and 900 bar. The reaction time is 100 minutes.

(b) After completion of the reaction the mixture is cooled to −5° C. and the gas phase is cautiously let down. The off-gas contains no 1,3-butadiene, ie. the conversion is quantitative. On cooling, the reactor contents separate into 2 phases. 224 g of a phase of lower density (upper phase) are formed, containing the following percentage proportions, based on material discharged from the reactor:

| 2.2 | wt. % of cobalt |
| 70 | wt. % of the pyridine |
| 82 | wt. % of the pentenoic acid ester |
| 45 | wt. % of the methanol |
| 95 | wt. % of the $C_4$-cut |

The phase of greater density (lower phase), amounting to 64 g, contains the following proportions, based on material discharged from the reactor:

| 97.8 | wt. % of cobalt |
| 18 | wt. % of the pentenoic acid ester |
| 30 | wt. % of the pyridine |
| 55 | wt. % of the methanol |
| 5 | wt. % of the $C_4$-cut |

(c) It follows from the above analysis that virtually the entire cobalt employed in stage (a) is present in the lower phase. 70% by volume of the lower phase, of greater density (corresponding to about 70% of the amount of cobalt) are recycled to stage (a) and fresh cobalt in the form of cobalt carbonyl is added, so as to obtain a ratio of 1,3-butadiene:cobalt of 1:0.1, which corresponds to 2.5 times the ratio described under section (a).

(d) If the molar ratios of the remaining components involved in the reaction have the same values as in stage (a), and the carbonylation is carried out at 135° C. and 900 bar, a reaction time of 55 minutes results, ie. the reaction rate has increased by a factor of 2.

We claim:
1. In a process for the preaparation of dimethyl butanedicarboxylates, wherein
   (a) butadiene or a hydrocarbon mixture containing butadiene is reacted with carbon monoxide and methanol in the presence of a tertiary nitrogen base and a cobalt carbonyl catalyst at from 80° to 150° C. under superatmospheric pressure,

(b) the greater part of the tertiary nitrogen base and any excess hydrocarbons are removed and (c) the methyl pentenoate thus obtained is reacted with carbon monoxide and methanol, in the presence of a cobalt carbonyl catalyst and the residual amount of tertiary nitrogen base, at from 140° to 200° C. under superatmospheric pressure, to give the dimethyl butanedicarboxylate, the improvement that the reaction mixture obtained in stage (a) after reaction of the butadiene is cooled until it separates into two phases, and a part-stream of from 20 to 80% by volume of the lower phase is recycled to stage (a).

2. The process of claim 1, wherein the reaction mixture from stage (a) is cooled to from −10° C. to +40° C.

3. The process of claim 1, wherein a molar ratio of methyl pentenoate to methanol of from 1:0.05 to 1:0.5 is maintained in the phase separation.

4. The process of claim 1, wherein the reaction mixture from stage (a) is cooled to from −5° to +20° C.

5. The process of claim 1, wherein a part-stream of from 50 to 80% by volume of the lower phase is recycled to stage (a).

* * * * *